United States Patent [19]

Lenselink et al.

[11] Patent Number: 5,015,761
[45] Date of Patent: May 14, 1991

[54] TRICYCLO{6.2.1.0$^{1,6}$}UNDECANES USEFUL AS FRAGRANCE CHEMICALS

[75] Inventors: Willem Lenselink, Voorthuizen; Gerben Sipma, Hoevelaken, both of Netherlands

[73] Assignee: PFW(Nederland)B.V., Amersfoort, Netherlands

[21] Appl. No.: 282,821

[22] Filed: Dec. 5, 1988

Related U.S. Application Data

[62] Division of Ser. No. 193,996, Oct. 6, 1980, abandoned.

[30] Foreign Application Priority Data

Oct. 9, 1979 [GB] United Kingdom ............. 7934984

[51] Int. Cl.$^5$ ............................................. C07C 67/02
[52] U.S. Cl. ..................................... 560/256; 512/15; 549/339; 558/429; 560/117; 568/343; 568/373; 568/446; 568/665; 568/817
[58] Field of Search .................... 260/256; 568/817

[56] References Cited

U.S. PATENT DOCUMENTS 2,933,506 5/1956 Ohloff ............................... 260/343.2
4,373,108 2/1983 Light ..................................... 568/817

OTHER PUBLICATIONS

Letter dated Oct. 14, 1988 in Interference 101,264 by Ian A. Calvert acting on the authority of the Commissioner.
Letter dated Oct. 14, 1988 in Interference 101,353 by Ian A. Calvert acting on the authority of the Commissioner.
Agreement dated Jul. 20, 1988 between PFW and IFF.

*Primary Examiner*—Michael L. Shippen
*Attorney, Agent, or Firm*—Dale R. Lovercheck

[57] ABSTRACT

Novel tricycloundecanones are disclosed having the general formula

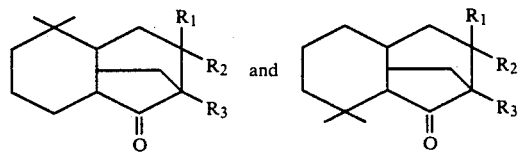

wherein $R_1$, $R_2$, and $R_3$ are hydrogen or 1 to 3 carbon alkyl groups having a total carbon number of six or less. These compounds are useful perfumery ingredients characterized by odors of the woody type.

Useful derivatives of the compounds are also disclosed as well as a novel procedure for preparation thereof.

4 Claims, No Drawings

TRICYCLO{6.2.1.0$^{1,6}$}UNDECANES USEFUL AS FRAGRANCE CHEMICALS

This application is a division of application Ser. No. 193,996 filed Oct. 6, 1980, now abandoned.

This invention relates to new chemical compounds useful as perfumes or as components of perfumes. Specifically it relates to compounds based on the skeleton of tricyclo{6.2.1.0$^{1,6}$}undecane. In a specific embodiment, the invention relates to a novel tricycloundecanone. In the fragrance industry there is a continuous search for new and useful synthetic fragrance materials. In the past mainly fragrance materials of natural origin were applied. Nowadays synthetic chemical compounds are used at an everincreasing rate. Such compounds may offer many advantages over natural products as essential oils and derivatives thereof or materials of animal origin. For example synthetic products are not or far less sensitive to factors as availability, price, quality, crop failure, adulteration and organoleptic reproducibility. It is also for these reasons that, especially in the field of expensive natural oils with highly useful woody odors, much effort is being made to find synthetic replacements.

It is the object of this invention to provide the novel chemical compounds dimethyltricyclo{6.2.1.0$^{1,6}$}undecanone-7 and certain lower alkyl derivatives thereof of the formulae

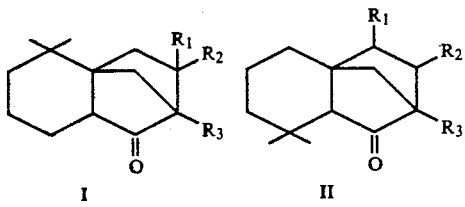

wherein $R_1$, $R_2$, and $R_3$ represent hydrogen or alkyl radicals of 1 to 3 carbon atoms and the total carbon number of $R_1$, $R_2$, and $R_3$ combined is 6 or less. These compounds are useful perfumery chemicals in themselves and are also useful as intermediates in the formation of other compounds which are likewise desirable perfumery chemicals. These compounds are characterized by odors of the woody type useful in a large variety of perfume types. They are obtainable, as explained hereinafter by a relatively simple, but novel synthesis from readily available, inexpensive starting materials.

In accordance with this invention, it has been found that the novel tricycloundecanones of the above formula can be prepared by a simple acid treatment of an oxo compound of the formula

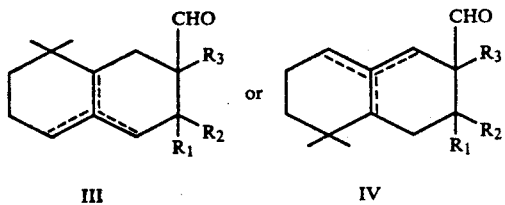

wherein $R_1$, $R_2$ and $R_3$ are as defined above and the dotted lines represent one carbon-carbon double bond. The acid treatment is carried out by maintaining the oxo compound in an acid environment created by the presence of a proton acid or a Lewis acid, for a period of time sufficient to cause the oxo compound to undergo a skeletal rearrangement to the dimethyltricycloundecanone.

As stated, the acid environment by which the skeletal rearrangement is caused to take place can be created by either proton or Lewis acids. Proton acids which can be used include lower organic acids such as formic acid and acetic acid, halogenated alkanoic acids such as mono-, di- or trichloroacetic acid, sulphonic acids such as metahnesulphonic acid, p-toluenesulphonic acid or sulphonated ion exchange resins and mineral acids such as hydrochloric acid, sulphuric acid, phosphoric acid, perchloric acid and boric acid or combinations of two or more acids. Lewis acids such as aluminum chloride, boron trifluoride, zinc chloride, tin tetrachloride and titan chlorides can also be used. The amount of acid to be used may vary from a catalytical amount to a molar excess. The acid treatment of the oxo compounds using Lewis acids is effected in the presence of an inert solvent at a relatively low temperature. Generally a temperature between about 50° C. and −50° C. is employed. The reaction takes place over a period of several hours. Solvents which can be employed include hydrocarbons such as hexane and cyclohexane, chlorinated hydrocarbons such as methylene chloride and 1,2-dichloroethane, aromatic solvents such as benzene, toluene, chlorobenzene and nitrobenzene and nitroalkanes such as nitroethane. When the acid treatment of the oxo-compound is effected with a proton acid generally elevated temperatures are employed. Here again the reaction takes place over a period of several hours. In the case a solvent is used, the reaction is conveniently carried out at reflux temperature. The solvents may be the same as the ones used for the reaction carried out in the presence of Lewis acids.

The oxo compounds of formulae III and IV which are subjected to acid treatment according to this invention can be prepared via a sequence of reactions known to the art. In the first step of a preferred reaction sequence myrcene (7-methyl-3-methylene-1,6-octadiene) is reacted via a Diels-Alder reaction with an α,β-unsaturated oxo compound of formula V to form the intermediate oxo compounds VI and VII.

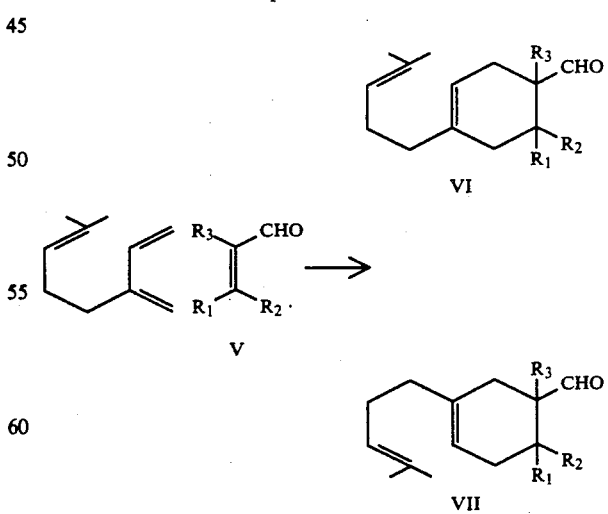

The Diels-Alder reaction can be conducted thermally, for example as described by G. Ohloff, Ann. 606 (1957), page 100. It can also be catalyzed by Lewis acids as taught by Wollweber, Diels-Alder Reactions, George Thieme Verlag, Stuttgart (1972), chapter A V, or by Netherlands patent application 79.09668. The reaction modification used for the condensation can influence the ratio of isomers VI and VII. Usually the formation of isomer VI is favored in the Lewis acid catalyzed modification.

Ring closure of the carbon skeleton of the aldehydes VI and VII to the octaline configuration can be accomplished as taught by G. Ohloff l.c., for example with protection of the aldehyde moiety of the molecule by means of Schiff's base derivatives.

The novel tricyclo{6,2,1,0$^{1,6}$}undecanones of formulae I and II can be further derivatized to convert them to other perfumery compounds. Specifically the compounds can be converted by derivatization of the oxo group to compounds of the formula

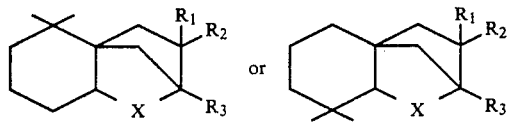

VIII                IX where $R_1$, $R_2$ and $R_3$ are as defined above and X is selected from:

(a)

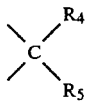

wherein $R_4$ is hydrogen, an alkyl, an alkenyl radical, or an alkoxy radical and $R_5$ is hydrogen, a hydroxy, an alkoxy, an alkanoyloxy or a cyanoalkoxy radical and the total number of carbon atoms of $R_4$ and $R_5$ combined is 8 or less.

(b)

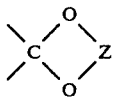

wherein Z represents an alkylene group of 6 carbon atoms or less.

(c)

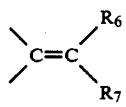

wherein $R_6$ is hydrogen or an alkyl radical and $R_7$ represents hydrogen or a formyl, alkanoyl, carboalkoxy or cyano group and the total number of carbon atoms of $R_6$ and $R_7$ combined is 4 or less; and (d)

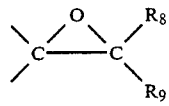

wherein $R_8$ is hydrogen or an alkyl radical and $R_9$ represents a cyano or a carboalkoxy group and the total number of carbon atoms of $R_8$ and $R_9$ combined is 4 or less.

These derivatives are readily prepared by methods known to the art, for example by Grignard reactions; reduction to an alcohol (chemically or catalytically), optionally followed by esterification; etherification; ketalization; Wittig reactions and modifications thereof; condensations with activated hydrogen compounds such as aldol condensations; Knoevenagel condensations; or Darzens condensations.

It will be apparent that the compounds of formulae I and II and the derivatives thereof can exist in a cis and trans stereochemical configuration with respect to the decalin (bicyclo{4.4.0}-decane) moiety of the molecules.

The treatment under acidic conditions of the compounds of formulae III and IV according to the invention gives rise to the formation of the compounds I and II wherein the decalin moiety exists predominantly in the cis-configuration. On a subsequent alkaline treatment this cis-configuration can be isomerized to the corresponding trans decalin configuration. Furthermore, it will be apparent that the substituents $R_1$, $R_2$, $R_4$ and $R_5$ of the compounds of the invention can be in an exo- or endo-position with regard to the norbornane (bicyclo{2.2.1}heptane) moiety of the molecules whereas the substituents $R_6$ and $R_7$ can be in an E- or Z-position with respect to the double bond to which they are attached.

Whenever a general structural formula is presented in this text or in the attached claims, it is intended to include all such stereoisomeric forms. The novel compounds of the invention exhibit a variety of useful odor nuances. The tricyclo{6,2,1,0$^{1,6}$}undecanones can be characterized as green, camphoraceous woody. The derivatives of the type (a), (b), (c) and (d) exhibit a range of characteristics including woody, cuminic, camphoraceous and ambery notes.

The novel compounds can be used as fragrances per se or as components of a fragrance composition. The term "fragrance composition" is used to denote a mixture of compounds including, for example, natural oils, synthetic oils, alcohols, aldehydes, ketones, esters, lactones, ethers, hydrocarbons and other classes of chemical compounds which are admixed so that the combined odors of the individual components produce a pleasant or desired fragrance. Such fragrance compositions or the novel compound of this invention alone can be used in conjunction with carriers, vehicles or solvents containing also, as needed, dispersants, emulsifiers, surface-active agents, aerosols propellants and the like. In fragrance compositions the individual components contribute their particular olfactory characteristics, but the overall effect of the composition is the sum of the effect of each ingredient. Thus, the compounds of this invention can be used to alter, enhance, or reinforce the aroma characteristics of the other natural or synthetic materials making up the fragrance composition, for example, by highlighting or moderating the olfactory reaction contributed by another ingredient or combination of ingredients.

The amount of the compounds of the invention which will be effective depends on many factors including the characteristics of the other ingredients, their amounts and the effects which are desired. It has been found that as little as 0.01% by weight of compounds of this invention can be used to alter the effect of a fragrance composition on cost, nature of end-product, the effect desired in the finished product, and the particular fragrance sought, but will usually not be more than about 50% by weight.

The compounds disclosed herein can be used in a wide variety of applications such as, e.g., detergents and soaps; space deodorants, perfumes, colognes; after-shave lotions; bath preparations such as bath oil and bath salts; hair preparations such as lacquers; brilliantines, pomades and shampoos; cosmetic preparations such as creams, deodorants, hand lotions, and sun screens; powders such as talcs, dusting powders, face powder; as masking agents, e.g., in household products such as bleaches, and in technical products such as shoe polish and automobile wax.

The following examples illustrate the invention. In all examples, unless otherwise specified, $R_1$, $R_2$, $R_3$, $R_4$, $R_5$, $R_6$, $R_7$ and $R_8$ can be taken to be hydrogen.

EXAMPLE 1

A mixture of 90 g formic acid, 10 g 85% phosphoric acid and 50 g (0.260 mole) of a 70:30 mixture of the compounds III and IV was refluxed for 2½ hours. After cooling to room temperature 100 ml water was added and the mixture was extracted twice with ether. The organic layer was washed with saturated NaCl solution and saturated KHCO$_3$ solution and dried with Na$_2$SO$_4$. Distillation yielded 44% of the compounds of formulae I and II, b.p. 96°-98° C. at 1 mm Hg, $n_D^{20}=1.5048$, with camphoraceous, minty, greenish woody odour.

IR (neat), cm$^{-1}$: 2920, 2875, 1744, 1463, 1452, 1386, 1367, 1347, 1306, 1293, 1278, 1236, 1194, 1178, 1100, 1076, 1046, 1036, 1022, 980, 926, 905, 863, 856, 700, 566, 508, 492, 449.

Proton-NMR (in CDCl$_3$), δ of characteristic absorption in ppm against TMS as internal standard: 0.97 (s, 3H), 1.03 (s, 3H), 2.57 (d, 1H).

EXAMPLE 2

50 g (0.260 mole) of a 70:30 mixture of the compounds III and IV was added in the course of 2½ hours to a mixture of 34.7 g (0.26 mole) aluminum chloride and 450 ml methylene chloride at 0° C. After an additional stirring period of 10minutes at 0° C. the reaction mixture was added to 150 g crushed ice. The organic layer was worked up as in Example 1. Distillation yielded 70% of the compounds of formula I and II, b.p. 89°-92° C. at 0.6 mm Hg, $n_D^{20}=1.5002$, with odour similar to that of Example 1.

EXAMPLE 3

Analogously to Example 2 at a reaction temperature of 20° C. was prepared a mixture of compounds I and II wherein $R_2$ is methyl from the corresponding compounds III and IV in 58% yield, b.p. 80°-85° C. at 0.2 mm Hg, $n_D^{20}=1.4955$, with dry cuminic, camphoraceous woody odour.

EXAMPLE 4

Analogously to Example 2 at a reaction temperature of −10° C. was prepared a mixture of compounds I and II wherein $R_3$ is methyl from the corresponding compounds III and IV in 82% yield, b.p. 85°-90° C. at 0.2 mm Hg, $n_D^{20}=1.4929$, with green camphoraceous woody odour.

EXAMPLE 5

Analogously to Example 1 was prepared a mixture of the compounds I and II wherein $R_2$ is ethyl and $R_3$ is methyl from the corresponding compounds III and IV in 60% yield, b.p. 97°-99° C. at 0.4 mm Hg, $n_D^{20}=1.4969$, with woody odour.

EXAMPLE 6

Analogously to Example 1 was prepared a mixture of the compounds I and II wherein $R_2$ is n-propyl from the corresponding compounds III and IV in 65% yield, b.p. 122°-124° C. at 1 mm Hg, $n_D^{20}=1.4966$, with fatty woody odour.

EXAMPLE 7

31 g (0.161 mole) of the compounds I and II as prepared in Example 2 wherein the decalin moiety predominantly is in the cis-configuration, was isomerised by treatment with a solution of 10 g potassium hydroxide in 100 ml methanol at 70° C. for one hour. Obtained was 85% yield of the compounds I and II wherein the decalin moiety is in the trans-configuration, b.p. 100°-105° C. at 0.5 mm Hg, $n_D^{20}=1.4976$, with green camphoraceous woody odour.

EXAMPLE 8

Analogously to Example 7 a mixture of the compounds I and II with cis-decalin moieties as prepared in Example 3 was isomerised to the corresponding compounds with trans-decalin configuration, b.p. 82°-85° C. at 0.1 mm Hg, $n_D^{20}=1.4970$, with an odour similar to that of Example 3.

EXAMPLE 9

20 g (0.104 mole) of the compounds as prepared in Example 1 was reacted with 1.2 g (0.033 mole) sodium borohydride in a mixture of 27 ml ethanol and 8 ml water at 50° C. for two hours. The cooled reaction mixture was acidified with 1% HCl solution and extracted with ether. The organic layer was washed with saturated KHCO$_3$ solution and saturated NaCl solution and dried with Na$_2$SO$_4$.

After evaporation of the solvent the residue was crystallized from n-hexane yielding 50% of the compounds of formulae VIII and IX wherein X represents

m.p. 112°-113° C., with woody odour.

EXAMPLE 10

Analogously to Example 9 was prepared a mixture of the compounds VIII and IX wherein $R_2$ is methyl and X represents

from the compounds as prepared in Example 3 in 89% yield, b.p. 110°-112° C. at 0.3 mm Hg, m.p. 80°-82° C., with woody odour.

EXAMPLE 11

20 g (0.104 mole) of the compounds I and II as prepared in Example 2 was added in 15 minutes at −5° C. to a solution of methylmagnesium iodide prepared from 3.9 g (0.161 grat.) magnesium and 25 g (0.176 mole) methyl iodide. The reaction mixture was stirred for 2 hours at room temperature and decomposed with a saturated ammonium chloride solution followed by ether extraction. The organic layer was washed with saturated KHCO$_3$ solution and saturated NaCl solution and dried with Na$_2$SO$_4$. Distillation yielded 74% of the compounds VIII and IX, wherein X represents

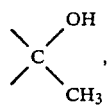

b.p. 93°-95° C. at 0.5 mm Hg, m.p. 75°-76° C., with woody odour.

EXAMPLE 12

9 g (0.046 mole) of the compounds as prepared in Example 9 was esterified by the action of 4.2 g formic acid and 9.4 g acetic anhydride at 50° C. for two hours. Distillation yielded 83% of the compounds of formulae VIII and IX wherein X represents

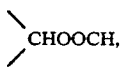

b.p. 76°-78° C. at 0.2 mm Hg, n$_D^{20}$=1.4971, with musty woody odour.

EXAMPLE 13

5 g (0.026 mole) of the compounds as prepared in Example 9 was treated with 20 g (0.196 mole) acetic anhydride and two drops of 85% phosphoric acid in 50 ml toluene at 40° C. for three hours. After washing neutral with saturated KHCO$_3$ solution, distillation yielded 73% of the compounds of formulae VIII and IX wherein X represents

b.p. 86°-87° C. at 0.3 mm Hg, n$_D^{20}$=1.4919, with ambery woody odour.

EXAMPLE 14

Analogously to Example 13 was prepared a mixture of compounds VIII and IX wherein R$_2$ is methyl and X represents

from the compounds as prepared in Example 10 in 91% yield, b.p. 81°-83° C. at 0.1 mm Hg, n$_D^{20}$=1.4869, with ambery woody odour.

EXAMPLE 15

To a suspension of 0.84 g (0.028 mole) 80% sodium hydride in 50 ml N,N-dimethylformamide was added in 15 minutes at 20° C. a solution of 5.5 g (0.028 mole) of the compounds VIII and IX as prepared in Example 9. After 3 hours at 20° C. the mixture was neutralised with acetic acid, diluted with 100 ml water and extracted with ether with saturated KHCO$_3$ solution, saturated NaCl solution and dried with Na$_2$SO$_4$. Distillation yielded 77% of the compounds VIII and IX wherein X represents

b.p. 60° C. at 0.1 mm Hg, n$_D^{20}$=1.4921, with woody odour.

EXAMPLE 16

A mixture of 25 g (0.139 mole) of the compounds of Example 1, 10 g (0.161 mole) ethylene glycol, 0.5 g p-toluenesulphonic acid and 200 ml toluene was refluxed for 4 hours with azeotropic removal of the water formed. The mixture was washed neutral with a saturated KHCO$_3$ solution and dried with Na$_2$SO$_4$. Distillation yielded 59% of the compounds of formulae VIII and IX wherein X represents

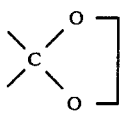

b.p. 77°-80° C. at 0.2 mm Hg, n$_D^{20}$=1.5041, with green camphoraceous woody odour.

EXAMPLE 17

To a suspension of 3.9 g (0.130 mole) 80% sodium hydride in 50 ml N,N-dimethyl formamide was added over a period of 20 minutes and at 30° C. 23 g (0.130 mole) of diethyl cyanomethylphosphonate. After an additional hour at 30° C., 25 g (0.130 mole) of the compounds of Example 1 was added in 15 minutes at 40° C. and the mixture was allowed to react for three hours at 40° C. The cooled reaction mixture was diluted with water and extracted with ether. The organic layer was washed neutral with water and dried with Na$_2$SO$_4$. Distillation yielded 68% of the compounds of formulae VIII and IX wherein X represents

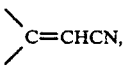

b.p. 100°-102° C. at 0.15 mm Hg, $n_D^{20}=1.5304$, with musty woody odour.

EXAMPLE 18

Analogously to Example 17 was prepared a mixture of the compounds VIII and IX wherein X represents

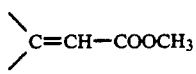

from the compounds of Example 1 and dimethyl carbomethoxymethylphosphonate in 60% yield, b.p. 105°-110° C. at 0.1 mm Hg, $n_D^{20}=1.5130$, with woody odour.

EXAMPLE 19

A perfume composition is prepared by admixing the following ingredients:
30 Ylang Ylang I
30 geranium Oil Bourbon
150 bergamot oil
150 gamma methylionone
150 phenylethyl alcohol
75 Lilial (Givaudan)
30 Lyral (IFF)
75 AC-1300 (PFW)
30 Celestolide (IFF)
45 Sandalwood oil
90 benzyl salicylate
15 undecylenic aldehyde 10%
15 styrallyl acetate
10 heliotropine
5 isoaugenol
15 eugenol
85 tricyclic compounds prepared according to Example 14.

The addition of the compounds of Example 14 gives a desired improvement of the odour profile.

What I claim and desire to protect by Letters Patent is:

1. A compound having the structure:

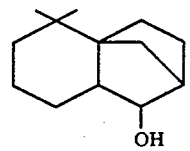

2. A compound having the structure:

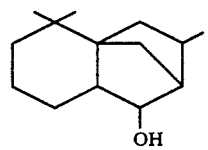

3. A compound having the structure:

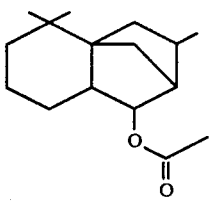

4. A compound having the structure:

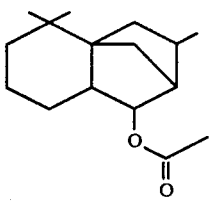

* * * * *

UNITED STATES PATENT AND TRADEMARK OFFICE
CERTIFICATE OF CORRECTION

PATENT NO. : 5,015,761

DATED : May 14, 1991

INVENTOR(S) : Willem Lenselink and Gerben Sipma

It is certified that error appears in the above-identified patent and that said Letters Patent is hereby corrected as shown below:

COLUMN 5, line 54: "10minutes" should be --10 minutes--;

COLUMN 8, line 18: after the word "ether" should be

--. The organic layer was washed--.

Signed and Sealed this

Third Day of November, 1992

*Attest:*

DOUGLAS B. COMER

*Attesting Officer*      *Acting Commissioner of Patents and Trademarks*